(12) United States Patent
Kelly

(10) Patent No.: US 7,223,875 B2
(45) Date of Patent: May 29, 2007

(54) PROCESS FOR MANUFACTURING PROPYLENE OXIDE

(75) Inventor: Michael D. Kelly, Memphis, TN (US)

(73) Assignee: Mobile Process Technology, Co., Memphis, TN (US)

( * ) Notice: Subject to any disclaimer, the term of this patent is extended or adjusted under 35 U.S.C. 154(b) by 641 days.

(21) Appl. No.: 10/741,066

(22) Filed: Dec. 19, 2003

(65) Prior Publication Data

US 2004/0138482 A1 Jul. 15, 2004

Related U.S. Application Data

(60) Provisional application No. 60/438,872, filed on Jan. 9, 2003.

(51) Int. Cl.
*C07D 301/19* (2006.01)

(52) U.S. Cl. ..................................... 549/529

(58) Field of Classification Search .............. 549/429, 549/529
See application file for complete search history.

(56) References Cited

U.S. PATENT DOCUMENTS

| | | | |
|---|---|---|---|
| 3,629,144 A | 12/1971 | Hahn et al. | |
| 3,931,044 A | 1/1976 | Maurin | |
| 4,405,572 A | 9/1983 | Moore et al. | |
| 4,626,596 A | 12/1986 | Marquis et al. | |
| 4,845,251 A | 7/1989 | Marquis et al. | |
| 5,093,509 A | 3/1992 | Meyer et al. | |
| 5,101,052 A | 3/1992 | Meyer et al. | |
| 5,354,460 A | 10/1994 | Kearney et al. | |
| 5,585,077 A | 12/1996 | Evans et al. | |
| 5,731,446 A | 3/1998 | Albal et al. | |
| 5,776,848 A | 7/1998 | Evans et al. | |
| 5,938,333 A | 8/1999 | Kearney | |

OTHER PUBLICATIONS

Kearney, M., Engineered Fractals Enhance Process Applications, Chemical Engineering Progress, Dec. 2000, pp. 61-68.

*Primary Examiner*—Bernard Dentz
(74) *Attorney, Agent, or Firm*—Ray F. Cox, Jr.

(57) ABSTRACT

A process for the recovery of molybdenum catalyst from the epoxidation reaction product of olefins with organic hydroperoxides. The active form of the glycol-molybdate epoxidation catalyst is removed from the process stream with an anion ion exchange resin. The ion exchange resin can be either a weak base or strong base type. The preferred embodiment of the invention produces a concentrated epoxidation catalyst in the "ammonium" form that is suitable for recycle to the catalyst preparation vessel. The ammonia form is converted into the active form by evaporating the water and ammonia from the recovered catalyst in the presence of a glycol. The preferred configuration of the ion exchange process is a "Lead-Lag" system. Two vessels will be in service while the third is in the regeneration mode recovering the epoxidation catalyst. A fourth polishing vessel can also be included as a "guard bed" to prevent leakage of the molybdate catalyst into the process stream. Since the ion exchange kinetics are slow compared to an aqueous system, the preferred embodiment uses a fractal fluid distribution system.

5 Claims, 3 Drawing Sheets

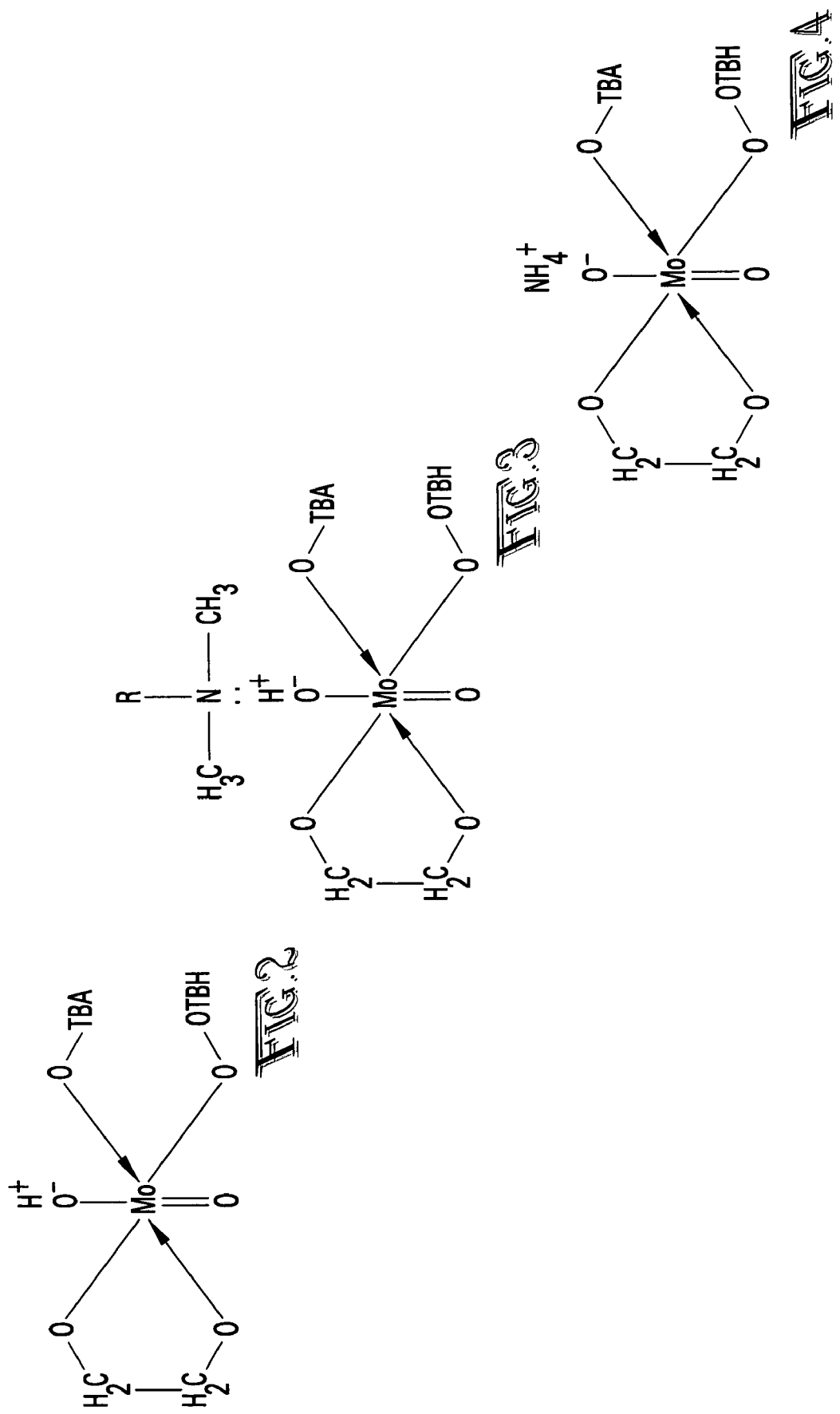

PROCESS FOR MANUFACTURING PROPYLENE OXIDE

CROSS-REFERENCE TO RELATED APPLICATIONS

This application claims the benefit of U.S. Provisional Application No. 60/438,872 filed Jan. 9, 2003, which is incorporated herein by reference.

STATEMENT REGARDING FEDERALLY SPONSORED RESEARCH OR DEVELOPMENT

Not applicable.

BACKGROUND OF THE INVENTION

1. Field of the Invention

The present invention relates to the recovery of molybdenum catalyst from the epoxidation reaction product of olefins with organic hydroperoxides, and in particular, to recovery of the molybdenum catalyst with an ion exchange process.

2. Brief Description of the Related Art

The epoxidation reaction of propylene with tertiary butyl hydroperoxide (TBH) in the presence of a catalyst produces propylene oxide and tertiary butyl alcohol (TBA). The reaction mixture from the epoxidation reaction comprises unreacted propylene, propylene oxide, TBA, unreacted TBH, the catalyst and impurities. The generic name for this reaction is the epoxidation of olefins with organic hydroperoxides. The reaction mixture may be separated by distillation to produce a recycled propylene fraction, a propylene oxide fraction, a recycled TBA fraction, and a fraction containing substantially all the dissolved catalyst along with various impurities.

The preferred epoxidation catalyst is a glycol-molybdate complex which is prepared by heating a mixture of an ammonium-containing molybdenum compound such as ammonium dimolybdate (ADM) and a glycol such as ethylene glycol (EG) or propylene glycol (PG) in an autoclave reactor. Ammonia and water by-products are driven from the reaction mixture as vapors and condensed and collected in the overheads condenser system. The glycol-molybdate complex is then used in the epoxidation reaction system.

The prepared catalyst is converted into the "active form" during the epoxidation reaction. During the distillation process to purify the TBA formed in the epoxidation reaction, the active form of the glycol-molybdate complex accumulates in the bottom of the distillation towers. The glycol-molybdate catalyst and other high boiling compounds are removed as a tarry mixture from the process by a residue evaporation system. The tarry bottoms material can cause severe heat transfer surface fouling requiring frequent outages for tube bundle cleaning and/or replacement.

Conventional methods for the recovery of molybdenum from the high boiler residue are disclosed in U.S. Pat. Nos. 3,629,144; 3,931,044; 4,405,572; 4,845,251; 5,093,509; 5,101,052; 5,585,077; 5,731,446; and 5,776,848, the disclosures of which are incorporated herein by reference. It is known to recover molybdenum from high boiler residue by incineration. It is believed that hydrometallurgy may able to extract molybdenum from the incineration fly ash.

The limitations of the prior art are overcome by the present invention as described below.

BRIEF SUMMARY OF THE INVENTION

The present invention is directed to a process that satisfies this need. The process comprises an improved propylene oxide manufacturing process in which the molybdenum catalyst is recovered by an ion exchange process.

The active form of the glycol-molybdate epoxidation catalyst is removed from the TBA process stream with an anion ion exchange resin. The ion exchange resin can be either a weak base or strong base type. The weak base is preferred because it regenerates very easily with ammonia or other bases such as but not limited to sodium hydroxide. The preferred embodiment of the invention produces a concentrated epoxidation catalyst in the "ammonium" form that is suitable for recycle to the catalyst preparation vessel. The ammonia form is converted into the active form by evaporating the water and ammonia from the recovered catalyst in the presence of a glycol such as EG or PG.

The preferred configuration of the ion exchange process is a "Lead-Lag" system which provides maximum removal efficiency. A third vessel is required to maintain the system on-stream 100% of the time. An any point in time, two vessels will be in service while the third is in the regeneration mode recovering the epoxidation catalyst. A fourth polishing vessel can also be included as a "guard bed" to prevent leakage of the molybdate catalyst into the TBA stream. The fourth polishing vessel provide a removal efficiency greater than 99%.

This new catalyst recovery process provides significant financial and environmental benefits to the olefin manufacturer. The removal of the epoxidation catalyst prior to the distillation of the TBA stream dramatically reduces the amount of molybdenum in the evaporator bottoms. The current process requires the off-site incineration of large volumes of tarry bottoms containing the epoxidation catalyst. The viscous tarry material also causes operating problems because of heat transfer surface fouling. The major identified benefits are reduced waste disposal, reduced process downtime, reduced maintenance costs, reduced purchases of molybdenum compounds, and improved TBA recovery yield.

These and other features, objects and advantages of the present invention will become better understood from a consideration of the following detailed description of the preferred embodiments and appended claims in conjunction with the drawings as described following:

BRIEF DESCRIPTION OF THE SEVERAL VIEWS OF THE DRAWINGS

FIG. 2 is a diagram of the proposed structure of the active form of the epoxidation catalyst.

FIG. 3 is a diagram of the proposed epoxidation catalyst bonded to an anion ion exchange resin.

FIG. 4 is a diagram of the proposed structure of the recovered epoxidation catalyst in the ammonium form.

DETAILED DESCRIPTION OF THE INVENTION

With reference to FIGS. 1-5, the preferred embodiment of the present invention may be described as follows.

Figure 1:
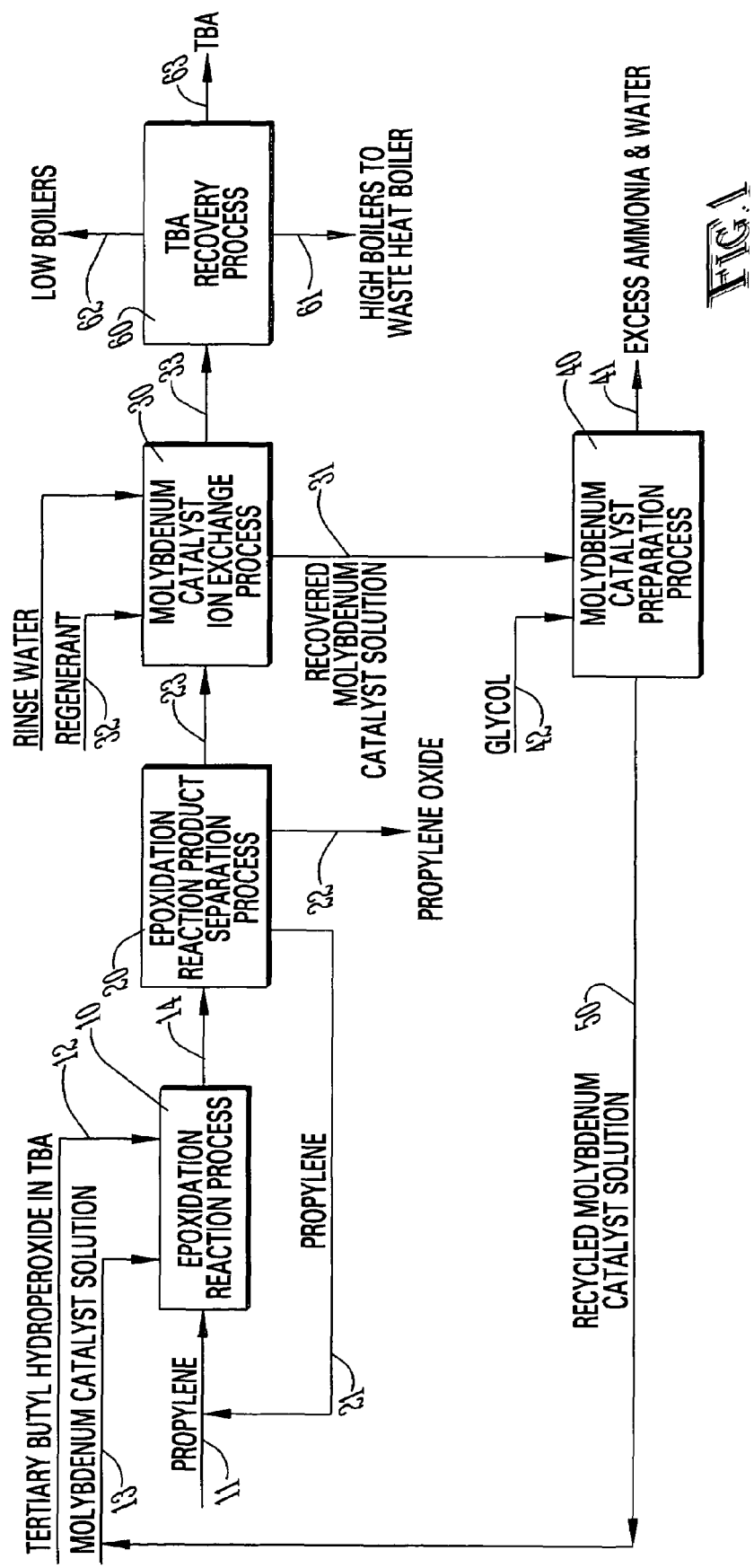
FIG. 1 is a flow diagram of the improved propylene oxide manufacturing process of the present invention with ion exchange molybdenum catalyst recovery by ion exchange.

With reference to FIG. 1, the epoxidation reaction process 10 reacts a propylene stream 11 with a tertiary butyl hydroperoxide (TBH) in tertiary butyl alcohol (TBA) stream 12 in the presence of a molybdenum catalyst 13 to produce a reaction product stream 14 containing unreacted propylene, propylene oxide, TBA, unreacted TBH, molybdenum catalyst and impurities. The reaction mixture 14 is separated in an epoxidation reaction product separation process 20 to produce a recycled propylene stream 21, a propylene oxide stream 22 and and TBA process stream 23 containing TBA, the dissolved molybdenum catalyst in the active form and various impurities. The "active form" of the molybdenum is shown in FIG. 2. The molybdenum catalyst is converted into the "active form" during the epoxidation reaction.

In accordance with the present invention, the active form of the molybdenum catalyst is removed from the TBA process stream 23 in a molybdenum catalyst ion exchange process 30. The ion exchange process comprises 30 an anion ion exchange resin. The ion exchange resin can be either a weak base or strong base type. The weak base is preferred because it regenerates very easily with ammonia or other bases such as but not limited to sodium hydroxide.

Examples of weak base ion exchange resins that can be utilized for the removal of the molybdenum epoxidation catalyst are resins that are composed of a crosslinked polyacrylate polymer matrix with a tertiary amine functional group, including but not limited to, Rohm & Haas IRA 67, Purolite A100, Bayer AP-40, Lewatit VP1072 and Diaion WA10; resins that are composed of a crosslinked polystyrene matrix and a tertiary amine functional group, including but not limited to, Rohm & Haas A21, Dowex 66, ResinTech WBMP and Lewatit MP62; resins that are composed of a crosslinked phenolic polymer matrix with a tertiary amine functional group, including but not limited to, Rohm & Haas A561; or resins that are composed of a crosslinked 4-vinyl pyridine polymer matrix with tertiary amine characteristics, including but not limited to, Reilex HP. Other crosslinked polymers are acceptable provided they include a weak base tertiary amine functional group.

The bonding of the molybdenum catalyst to the ion exchange resin is shown in FIG. 3. The active form of the molybdenum epoxidation catalyst contains a strongly acidic proton which "protonates" the weak base ion exchange resin (see U.S. Pat. No. 4,626,596, col. 8, lines 12-14, the entire disclosure of which is incorporated herein by reference). This reaction is analogous to the conventional use of weak base anion resins for removing strong mineral acids. The weak base is the preferred ion exchange resin because it can be regenerated with aqueous ammonium hydroxide. Other bases can be used, including but not limited to, sodium hydroxide or potassium hydroxide. Ammonium hydroxide is preferred because it allows for the recycle of the catalyst after the ammonia and water are evaporated in the presence of ethylene glycol (EG). When ammonium hydroxide is the regenerant 32, the recovered molybdenum catalyst solution is concentrated in the "ammonium" form that is suitable for recycle directly to the molybdenum catalyst preparation process 40.

The preferred invention produces a recovered molybdenum catalyst solution stream 31, where the concentrated molybdenum catalyst solution is in the ammonium form as shown in FIG. 4. The recovered molybdenum catalyst solution stream 31 is suitable for recycle to the molybdenum catalyst preparation process 40. The ammonium form of the molybdenum catalyst is converted into the active form by evaporating the water and ammonia 41 from the recovered molybdenum catalyst solution in the presence of a glycol 42, such as ethylene glycol, propylene glycol or other glycols that will form a complex with molybdenum. (See U.S. Pat. No. 4,626,596, which is incorporated herein by reference.) The recycled molybdenum catalyst solution stream 50 is recycled to the epoxidation reaction process 10.

The present invention removes essentially all of the molybdenum catalyst from the TBA process stream 23. The removal of the molybdenum catalyst from the TBA process stream 23 provides for several benefits in the manufacturing of propylene oxide. The benefits include but are not limited to (a) elimination in off-site residue disposal, (b) reduced purchases of molybdate salts used in the preparation of the molybdenum epoxidation catalyst (see U.S. Pat. No. 4,845,251, which is incorporated herein by reference), (c) improved distillation performance due to reduced fouling of downstream reboiler surfaces by the concentrated molybdenum catalyst and (d) improved energy efficiency because the residual high boiling bottoms fraction does not contain the molybdenum catalyst and therefore it can be used as a source of fuel in waste heat boilers.

The TBA effluent stream 33 from the molybdenum catalyst ion exchange process 30 contains essentially no molybdenum catalyst (less than 0.5 ppm). The TBA effluent process stream 33 is further purified by distillation in the TBA recovery process 60 to remove the high boiling residue stream 61 and the low boiling residue stream 62 to produce a purified TBA effluent stream 63. Since the molybdenum catalyst has been substantially removed from the TBA effluent stream 33, the resulting high boiling residue stream 61 can be burned in a waste heat boiler without concern of discharging low levels of molybdenum into the environment.

Figure 5:
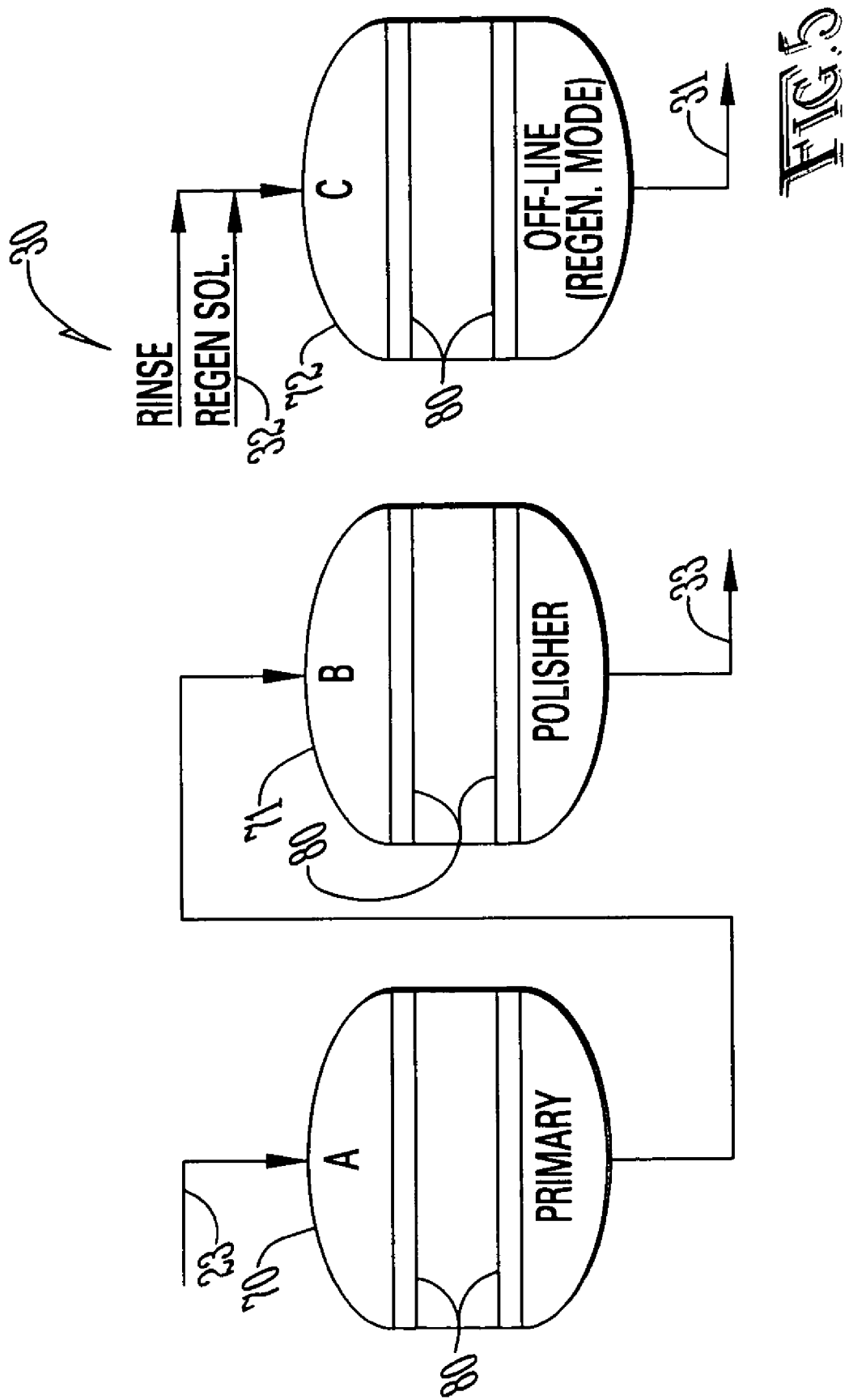
FIG. 5 is a diagram of a lead-lag ion exchange system.

The preferred configuration of the molybdenum catalyst ion exchange process 30 as shown in FIG. 5 is a "Lead-Lag" system, which provides maximum removal efficiency. The "Lead-Lag" system comprises a primary vessel 70 to receive the TBA process stream 23 and a polisher 71 which receives the effluent from the primary vessel 70. The effluent from the polisher 71 is the TBA effluent process stream 33. A third vessel 72 for off-line regeneration is required to maintain the system on-stream all of the time. At a given point in time, any two of the vessels will be in service while the third is in the regeneration mode recovering the molybdenum catalyst. A fourth polishing vessel can optionally be included as a "guard bed" to prevent leakage of the molybdate catalyst into the TBA stream. The fourth polishing vessel provides a removal efficiency greater than 99%.

The process chemistry of the TBA-molybdenum catalyst system is non-aqueous. Because of the non-aqueous nature of this system, the ion exchange kinetics are considerably slower than in aqueous systems. Conventional ion exchange systems use flow distribution hardware that utilizes slotted pipes or special screen wrapped pipes for the distribution of the process fluid (typically water). Conventional fluid distribution technology present problems for certain non-aqueous systems that require very low fluid velocities because of the inherently slow kinetics of the ion exchange process. In the case of the TBA-molybdenum removal ion exchange process, the kinetics are very slow and the use of a conventional fluid distribution system can result in channeling of the fluid resulting in leakage of molybdenum into the TBA effluent stream 33. The preferred fluid distribution technology for the present invention utilizes fractal fluid engineering principles. (See U.S. Pat. No. 5,354,460, which is incorporated herein by reference). As shown in FIG. 5, the use of fractal flow distributors 80 provides for homogeneous flow though the entire cross section of ion exchange vessel

70, 71, 72 resulting in no channeling at very low fluid velocity as required by the TBA-molybdenum catalyst system. An additional advantage of using fractal fluid distribution systems is the high turndown ratio. The regeneration step of the present invention utilizes an aqueous solution of ammonium hydroxide and has relatively fast kinetics. The high turndown ratio of fractal fluid distribution systems allows for high fluid velocities during the regeneration step and low fluid velocities during the molybdenum removal process without changing the homogeneous liquid flow pattern.

The present invention has been described with reference to certain preferred and alternative embodiments that are intended to be exemplary only and not limiting to the full scope of the present invention as set forth in the appended claims.

What is claimed is:

1. In a process for the manufacture of propylene oxide by the epoxidation reaction in a tertiary butyl alcohol stream (TBA) of propylene with tertiary butyl hydroperoxide (TBH) in the presence of a molybdenum catalyst in the form of a glycol-molybdate complex to produce a reaction product stream comprising unreacted propylene, propylene oxide, tertiary butyl alcohol, unreacted TBH, molybdenum catalyst in the form of a glycol-molybdate complex and impurities, the improvement comprising the steps of:
    (a) separating the reaction product stream into a recycled propylene stream, a propylene oxide stream, and a TBA process stream;
    (b) passing the TBA process stream through an ion exchange process comprising a weak base anion ion exchange resin to remove substantially all the molybdenum catalyst; and
    (c) regenerating the ion exchange resin with ammonium hydroxide, whereby the molybdenum catalyst is regenerated from the anion ion exchange resin in the ammonium form.

2. The improved process of claim 1, comprising the additional steps following step (c) of converting the molybdenum catalyst in the ammonium form to the active form by evaporating water and ammonia in the presence of a glycol to produce a glycol-molybdate complex and recycling the glycol-molybdate catalyst to the epoxidation reaction.

3. The improved process of claim 2 wherein the glycol is selected from the group consisting of ethylene glycol and propylene glycol.

4. The improved process of claim 1 wherein the ion exchange process of step (a) is configured in a lead-lag configuration.

5. The improved process of claim 1 wherein the ion exchange process comprises a fractal fluid distribution system for distributing the TBA process stream into the anion ion exchange resin.

* * * * *